US012588885B2

(12) United States Patent
Takahashi

(10) Patent No.: US 12,588,885 B2
(45) Date of Patent: Mar. 31, 2026

(54) FAT MASS DERIVATION DEVICE, FAT MASS DERIVATION METHOD, AND FAT MASS DERIVATION PROGRAM

(71) Applicant: FUJIFILM Corporation, Tokyo (JP)

(72) Inventor: Tomoyuki Takahashi, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 359 days.

(21) Appl. No.: 17/822,688

(22) Filed: Aug. 26, 2022

(65) Prior Publication Data

US 2023/0102862 A1      Mar. 30, 2023

(30) Foreign Application Priority Data

Sep. 27, 2021    (JP) ................................. 2021-157098

(51) Int. Cl.
| | |
|---|---|
| *A61B 6/00* | (2024.01) |
| *A61B 5/00* | (2006.01) |
| *A61B 6/03* | (2006.01) |
| *A61B 6/46* | (2024.01) |

(52) U.S. Cl.
CPC .......... *A61B 6/5217* (2013.01); *A61B 5/4872* (2013.01); *A61B 6/032* (2013.01); *A61B 6/463* (2013.01)

(58) Field of Classification Search
CPC ..... A61B 6/5217; A61B 5/4872; A61B 6/032; A61B 6/463; A61B 6/5282; A61B 5/7267; A61B 6/4241
See application file for complete search history.

(56) References Cited

U.S. PATENT DOCUMENTS

| | | | |
|---|---|---|---|
| 2005/0209528 A1* | 9/2005 | Sato .................... | A61B 5/6887 600/547 |
| 2006/0074288 A1 | 4/2006 | Kelly et al. | |
| 2011/0075900 A1 | 3/2011 | Masumoto | |
| 2011/0158386 A1 | 6/2011 | Payne et al. | |
| 2011/0235886 A1* | 9/2011 | Kelly .................. | A61B 5/4872 378/62 |

(Continued)

FOREIGN PATENT DOCUMENTS

| | | |
|---|---|---|
| EP | 3501399 A1 | 6/2019 |
| JP | 2008-125728 A | 6/2008 |

(Continued)

OTHER PUBLICATIONS

An Office Action; "Notice of Reasons for Refusal," mailed by the Japanese Patent Office on Feb. 4, 2025, which corresponds to Japanese Patent Application No. 2021-157098 and is related to U.S. Appl. No. 17/822,688; with English language translation.

*Primary Examiner* — Amandeep Saini
*Assistant Examiner* — Emma Rose Goebel
(74) *Attorney, Agent, or Firm* — Studebaker Brackett PLLC

(57) ABSTRACT

A fat mass derivation device includes at least one processor, in which the processor derives a fat mass distribution of a subject from a first radiation image and a second radiation image acquired by imaging the subject with radiation having different energy distributions, and derives a visceral fat mass distribution of the subject based on a shape of the fat mass distribution in a cross section orthogonal to a body axis of the subject.

13 Claims, 12 Drawing Sheets

(56) References Cited

U.S. PATENT DOCUMENTS

| | | | | |
|---|---|---|---|---|
| 2012/0004570 A1* | 1/2012 | Shimizu | ................. | A61B 5/055 |
| | | | | 600/587 |
| 2013/0281820 A1* | 10/2013 | Payne | ..................... | A61B 6/50 |
| | | | | 600/407 |
| 2014/0025346 A1* | 1/2014 | Uchiyama | ............ | A61B 5/1072 |
| | | | | 703/1 |
| 2018/0263559 A1 | 9/2018 | Kawamura | | |
| 2018/0326149 A1 | 11/2018 | Lipschultz et al. | | |
| 2020/0178920 A1* | 6/2020 | Grasruck | ............... | A61B 6/545 |

FOREIGN PATENT DOCUMENTS

| | | | |
|---|---|---|---|
| JP | 2009-022576 A | 2/2009 |
| JP | 2011-092685 A | 5/2011 |
| JP | 2016-220850 A | 12/2016 |
| JP | 2017-093912 A | 6/2017 |
| JP | 2018-153605 A | 10/2018 |
| JP | 2020-519348 A | 7/2020 |

* cited by examiner

Gs y x

ENERGY SPECTRUM

RADIATION BEFORE BEING
TRANSMITTED THROUGH
HUMAN BODY

RADIATION AFTER BEING
TRANSMITTED THROUGH
FAT TISSUE

RADIATION AFTER BEING
TRANSMITTED THROUGH
MUSCLE TISSUE

ENERGY (keV)

FIG. 13

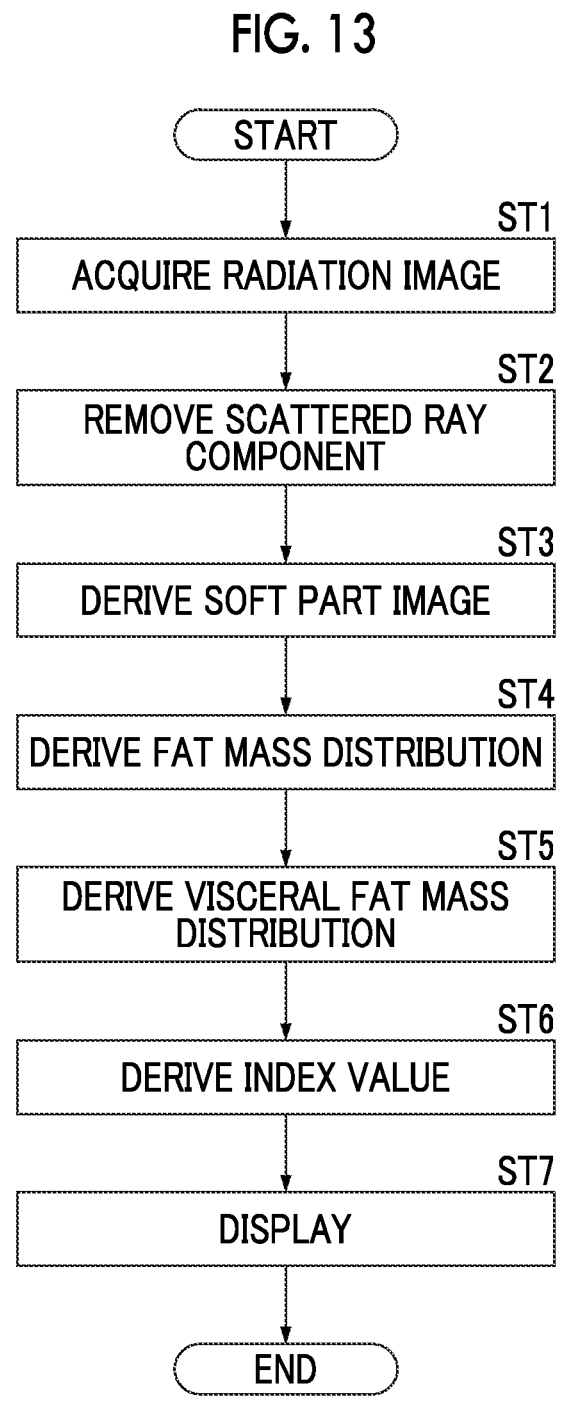

START

ST1

ACQUIRE RADIATION IMAGE

ST2

REMOVE SCATTERED RAY
COMPONENT

ST3

DERIVE SOFT PART IMAGE

ST4

DERIVE FAT MASS DISTRIBUTION

ST5

DERIVE VISCERAL FAT MASS
DISTRIBUTION

ST6

DERIVE INDEX VALUE

ST7

DISPLAY

END

FAT MASS DERIVATION DEVICE, FAT MASS DERIVATION METHOD, AND FAT MASS DERIVATION PROGRAM

CROSS REFERENCE TO RELATED APPLICATIONS

The present application claims priority under 35 U.S.C. § 119 to Japanese Patent Application No. 2021-157098 filed on Sep. 27, 2021. The above application is hereby expressly incorporated by reference, in its entirety, into the present application.

BACKGROUND

Technical Field

The present disclosure relates to a fat mass derivation device, a fat mass derivation method, and a fat mass derivation program.

Related Art

In order to prevent the occurrence of a cardiovascular disease (myocardial infarction, angina, cerebral infarction, arteriosclerosis obliterans, and the like) caused by hypertension, hyperglycemia, dyslipidemia, and the like, it is important to manage a body fat percentage. Therefore, a composition of fat in a human body is derived by energy subtraction processing using two radiation images obtained by irradiating a subject with two types of radiation having different energy distributions (see JP2018-153605A). In addition, a method has also been proposed in which a dual x-ray absorptiometry (DXA) method as one of typical bone mineral quantification methods used for diagnosing bone mineral density is used to calculate a body fat percentage in an osseous system disease, such as osteoporosis (see JP2016-220850A)

On the other hand, it has been clarified that the cardiovascular disease described above is caused by the accumulation of visceral fat. Therefore, a method has been proposed in which a computed tomography (CT) image is used to acquire a distribution of subcutaneous fat regions and a distribution of visceral fat regions in a region of the abdomen (see JP2009-022576A).

By using the CT image as disclosed in JP2009-022576A, a visceral fat mass distribution can be acquired. However, it takes a long time to capture the CT image, and an amount of exposure to the subject is large. Therefore, it is desired to acquire the visceral fat mass distribution more easily than a case of using the CT image.

SUMMARY OF THE INVENTION

The present disclosure is made in view of such circumstances, and is to make it possible to easily acquire the visceral fat mass distribution.

A fat mass derivation device according to the present disclosure comprises at least one processor, in which the processor derives a fat mass distribution of a subject from a first radiation image and a second radiation image acquired by imaging the subject with radiation having different energy distributions, and derives a visceral fat mass distribution of the subject based on a shape of the fat mass distribution in a cross section orthogonal to a body axis of the subject.

Note that, in the fat mass derivation device according to present disclosure, the processor may derive the fat mass distribution of the subject from the first radiation image and the second radiation image acquired by imaging the subject from a front surface or a rear surface, and may derive the visceral fat mass distribution by separating the fat mass distribution into a subcutaneous fat mass distribution and the visceral fat mass distribution based on a minimum point of the fat mass distribution and symmetry of the fat mass distribution.

In the fat mass derivation device according to present disclosure, the processor may derive an interval between at least one end part of the fat mass distribution and a maximum point closest to the end part as a subcutaneous fat thickness of the subject, and may derive the visceral fat mass distribution from the fat mass distribution based on the subcutaneous fat thickness.

In addition, in the fat mass derivation device according to present disclosure, the processor may derive the visceral fat mass distribution from the fat mass distribution by using a trained neural network, and the trained neural network may be trained by using teacher data including a fat mass distribution for learning and a visceral fat mass distribution which is a correct answer in the fat mass distribution for learning.

In addition, in the fat mass derivation device according to present disclosure, the processor may display a visceral fat image representing the visceral fat mass distribution.

In addition, in the fat mass derivation device according to present disclosure, the processor may acquire a past visceral fat image for the same subject, and may display the visceral fat image and the past visceral fat image in a comparable manner.

In addition, in the fat mass derivation device according to present disclosure, the processor may acquire a past visceral fat image for the same subject, and may display a change amount of the visceral fat image from the past visceral fat image.

In addition, in the fat mass derivation device according to present disclosure, the processor may derive an index value of visceral fat mass in a predetermined region of the subject based on the visceral fat mass distribution, and may display the index value.

In this case, the index value may be at least one of volume or weight of the visceral fat mass.

In addition, the index value may be a visceral fat percentage of the subject.

In addition, in the fat mass derivation device according to present disclosure, the processor may acquire a past index value which is at least one past index value of the subject, and may display a change of the index value based on the index value and the past index value as a graph.

In addition, in the fat mass derivation device according to present disclosure, the processor may derive a smoothed fat mass distribution.

A fat mass derivation method according to the present disclosure comprises deriving a fat mass distribution of a subject from a first radiation image and a second radiation image acquired by imaging the subject with radiation having different energy distributions, and deriving a visceral fat mass distribution of the subject based on a shape of the fat mass distribution in a cross section orthogonal to a body axis of the subject.

Note that a program causing a computer to execute the fat mass derivation method according to the present disclosure may be provided.

According to the present disclosure, the visceral fat mass distribution can be easily acquired.

BRIEF DESCRIPTION OF THE DRAWINGS

FIG. 13 is a flowchart showing processing performed in the first embodiment.

DETAILED DESCRIPTION

Figure 1:
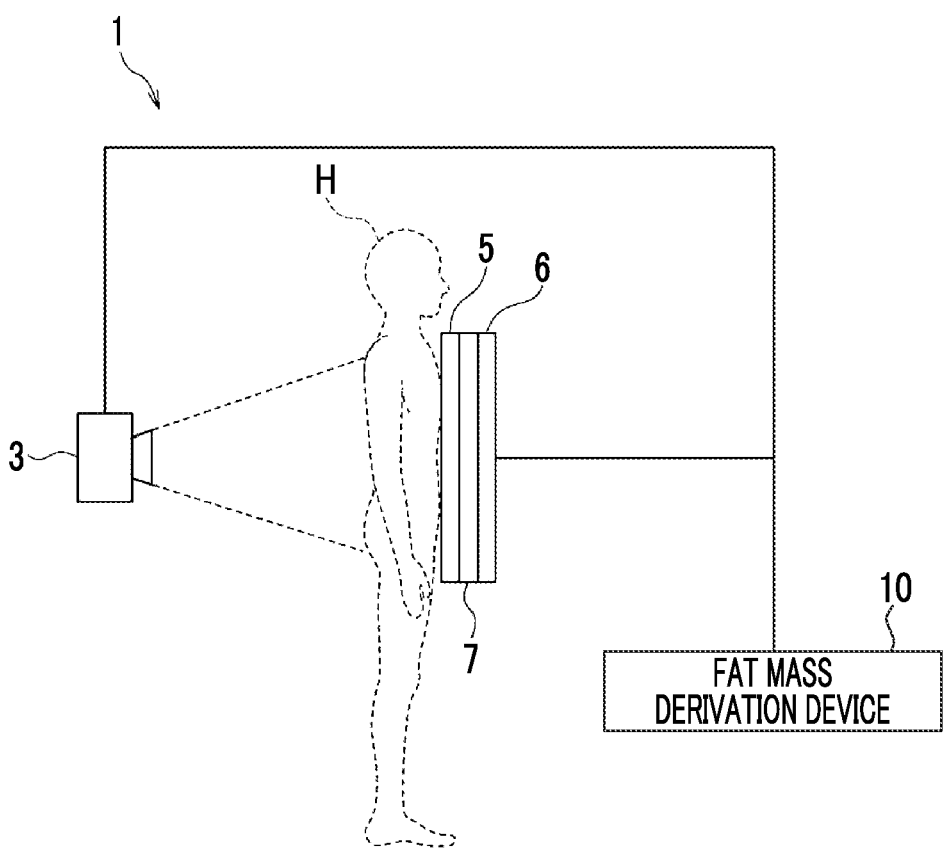
FIG. 1 is a schematic block diagram showing a configuration of a radiography system to which a fat mass derivation device according to a first embodiment of the present disclosure is applied.

Hereinafter, embodiments of the present disclosure will be described with reference to the drawings. FIG. 1 is a schematic block diagram showing a configuration of a radiography system to which a fat mass derivation device according to the embodiment of the present disclosure is applied. As shown in FIG. 1, the radiography system according to the present embodiment comprises an imaging apparatus 1, and a fat mass derivation device 10 according to the present embodiment.

The imaging apparatus 1 is an imaging apparatus that performs energy subtraction by a so-called one-shot method of converting radiation, such as X-rays, emitted from a radiation source 3 and transmitted through a subject H into energy and irradiating a first radiation detector 5 and a second radiation detector 6 with the converted radiation. During imaging, as shown in FIG. 1, the first radiation detector 5, a radiation energy conversion filter 7 consisting of a copper plate or the like, and the second radiation detector 6 are disposed in order from a side closest to the radiation source 3, and the radiation source 3 is driven. Note that the first and second radiation detectors 5 and 6 are closely attached to the radiation energy conversion filter 7.

As a result, in the first radiation detector 5, a first radiation image G1 of the subject H by low-energy radiation including so-called soft rays is acquired. In addition, in the second radiation detector 6, a second radiation image G2 of the subject H by high-energy radiation from which the soft rays are removed is acquired. The first and second radiation images G1 and G2 are input to the fat mass derivation device 10. Both the first and second radiation images G1 and G2 are front images including an abdomen of the subject H. Note that, although the radiation is emitted from a rear surface side of the subject H in FIG. 1, the radiation may be emitted from a front surface side of the subject H.

The first and second radiation detectors 5 and 6 can perform recording and reading-out of the radiation image repeatedly. A so-called direct-type radiation detector that directly receives irradiation with the radiation and generates an electric charge may be used, or a so-called indirect-type radiation detector that converts the radiation into visible light and then converts the visible light into an electric charge signal may be used. In addition, as a method of reading out a radiation image signal, it is desirable to use a so-called thin film transistor (TFT) readout method in which the radiation image signal is read out by turning a TFT switch on and off, or a so-called optical readout method in which the radiation image signal is read out by irradiation with read out light. However, other methods may also be used without being limited to these methods.

Figure 2:
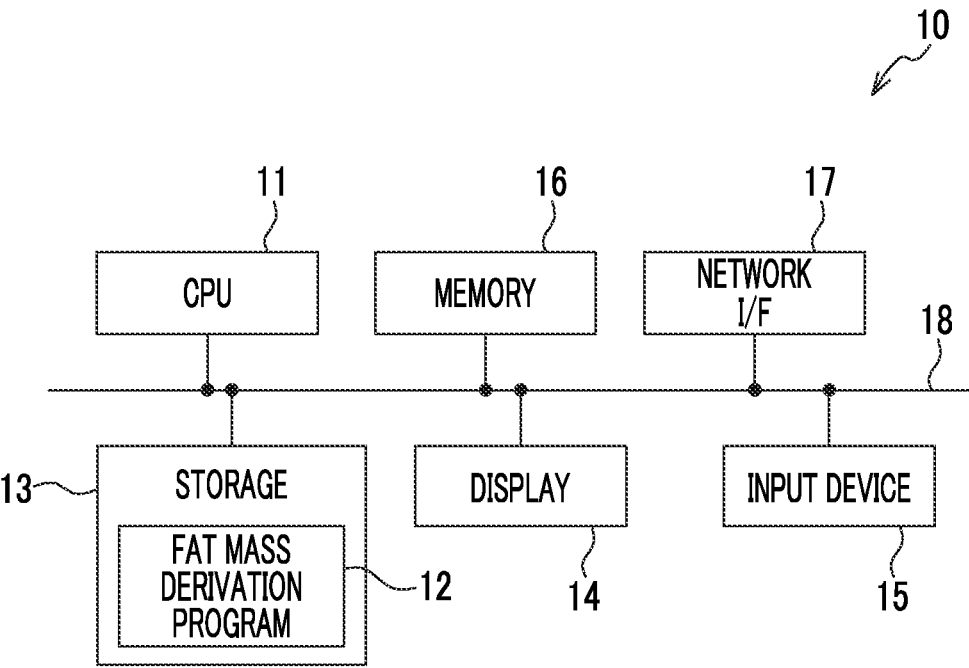
FIG. 2 is a diagram showing a schematic configuration of the fat mass derivation device according to the first embodiment.

Then, the fat mass derivation device according to the first embodiment will be described. First, a hardware configuration of the fat mass derivation device according to the first embodiment will be described with reference to FIG. 2. As shown in FIG. 2, the fat mass derivation device 10 is a computer, such as a workstation, a server computer, and a personal computer, and comprises a central processing unit (CPU) 11, a non-volatile storage 13, and a memory 16 as a transitory storage region. In addition, the fat mass derivation device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. Note that the CPU 11 is an example of a processor according to the present disclosure.

The storage 13 is realized by a hard disk drive (HDD), a solid state drive (SSD), a flash memory, and the like. A fat mass derivation program 12 installed in the fat mass derivation device 10 is stored in the storage 13 as a storage medium. The CPU 11 reads out the fat mass derivation program 12 from the storage 13, expands the read out fat mass derivation program 12 in the memory 16, and executes the expanded fat mass derivation program 12.

Note that the fat mass derivation program 12 is stored in a storage device of the server computer connected to the network or in a network storage in a state of being accessible from the outside, and is downloaded and installed in the computer that configures the fat mass derivation device 10 in response to the request. Alternatively, the fat mass derivation program 12 is distributed in a state of being recorded on a recording medium, such as a digital versatile disc (DVD) or a compact disc read only memory (CD-ROM), and is installed in the computer that configures the fat mass derivation device 10 from the recording medium.

Figure 3:
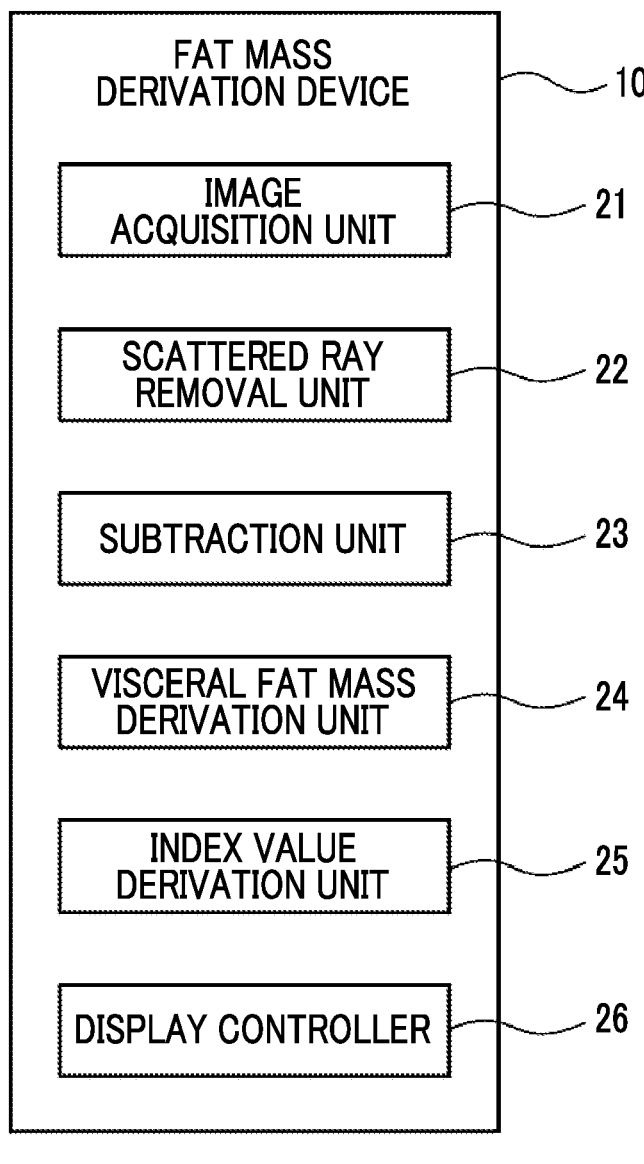
FIG. 3 is a diagram showing a functional configuration of the fat mass derivation device according to the first embodiment.

Then, a functional configuration of the fat mass derivation device according to the first embodiment will be described. FIG. 3 is a diagram showing a functional configuration of the fat mass derivation device according to the first embodiment. As shown in FIG. 3, the fat mass derivation device 10 comprises an image acquisition unit 21, a scattered ray removal unit 22, a subtraction unit 23, a visceral fat mass derivation unit 24, an index value derivation unit 25, and a display controller 26. Moreover, by executing the fat mass derivation program 12, the CPU 11 functions as the image acquisition unit 21, the scattered ray removal unit 22, the subtraction unit 23, the visceral fat mass derivation unit 24, the index value derivation unit 25, and the display controller 26.

The image acquisition unit 21 acquires the first radiation image G1 and the second radiation image G2 which are the front images of the subject H from the first and second radiation detectors 5 and 6 by causing the imaging apparatus 1 to perform energy subtraction imaging of the subject H. In a case in which the first radiation image G1 and the second radiation image G2 are acquired, imaging conditions, such as an imaging dose, a radiation quality, a tube voltage, a source image receptor distance (SID) which is a distance between the radiation source 3 and surfaces of the first and second radiation detectors 5 and 6, a source object distance (SOD) which is a distance between the radiation source 3 and a surface of the subject H, and the presence or absence of a scattered ray removal grid are set.

The SOD and the SID are used to calculate a body thickness distribution as described below. It is preferable that the SOD be acquired by, for example, a time of flight (TOF) camera. It is preferable that the SID be acquired by, for example, a potentiometer, an ultrasound range finder, a laser range finder, or the like.

The imaging conditions need only be set by input from the input device 15 by an operator.

Here, each of the first radiation image G1 and the second radiation image G2 includes a scattered ray component based on the radiation scattered in the subject H in addition to a primary ray component of the radiation transmitted through the subject H. Therefore, the scattered ray removal unit 22 removes the scattered ray component from the first radiation image G1 and the second radiation image G2. For example, the scattered ray removal unit 22 may remove the scattered ray component from the first radiation image G1 and the second radiation image G2 by applying a method disclosed in JP2015-043959A. In a case in which a method disclosed in JP2015-043959A or the like is used, the derivation of the body thickness distribution of the subject H and the derivation of the scattered ray component for removing the scattered ray component are performed at the same time.

Hereinafter, the removal of the scattered ray component from the first radiation image G1 will be described, but the removal of the scattered ray component from the second radiation image G2 can also be performed in the same manner. First, the scattered ray removal unit 22 acquires a virtual model of the subject H having an initial body thickness distribution $T0(x,y)$. The virtual model is data virtually representing the subject H of which a body thickness in accordance with the initial body thickness distribution $T0(x,y)$ is associated with a coordinate position of each pixel of the first radiation image G1. Note that the virtual model of the subject H having the initial body thickness distribution $T0(x,y)$ may be stored in the storage 13 of the fat mass derivation device 10 in advance. In addition, the scattered ray removal unit 22 may calculate a body thickness distribution $T(x,y)$ of the subject H based on the SID and the SOD included in the imaging conditions. In this case, the initial body thickness distribution $T0(x,y)$ can be obtained by subtracting the SOD from the SID.

Next, the scattered ray removal unit 22 generates, based on the virtual model, an image obtained by synthesizing an estimated primary ray image in which a primary ray image obtained by imaging the virtual model is estimated and an estimated scattered ray image in which a scattered ray image obtained by imaging the virtual model is estimated as an estimated image in which the first radiation image G1 obtained by imaging the subject H is estimated.

Next, the scattered ray removal unit 22 corrects the initial body thickness distribution $T0(x,y)$ of the virtual model such that a difference between the estimated image and the first radiation image G1 is small. The scattered ray removal unit 22 repeatedly performs the generation of the estimated image and the correction of the body thickness distribution until the difference between the estimated image and the first radiation image G1 satisfies a predetermined termination condition. The scattered ray removal unit 22 derives the body thickness distribution in a case in which the termination condition is satisfied as the body thickness distribution $T(x,y)$ of the subject H. In addition, the scattered ray removal unit 22 removes the scattered ray component included in the first radiation image G1 by subtracting the scattered ray component in a case in which the termination condition is satisfied from the first radiation image G1.

Figure 4:
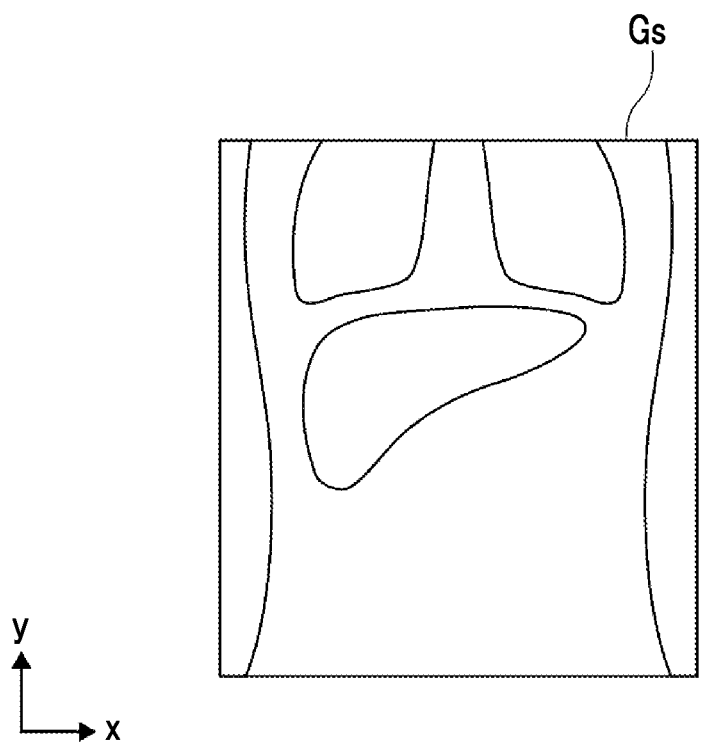
FIG. 4 is a diagram showing a soft part image.

The subtraction unit 23 derives a soft part image Gs obtained by extracting the soft part of the subject H from the first and second radiation images G1 and G2 by performing the energy subtraction processing. Note that, in the first and second radiation images G1 and G2 in the subsequent processing, the scattered ray component is removed. In a case in which the soft part image Gs is derived, the subtraction unit 23 performs weighting subtraction between the corresponding pixels with respect to the first and second radiation images G1 and G2 as shown in Expression (1) to generate the soft part image Gs in which the soft part of the subject H included in each of the radiation images G1 and G2 is extracted, as shown in FIG. 4. In Expression (1), $\alpha$ is a weighting coefficient. In the following description, a right-left direction of a paper surface of the soft part image Gs shown in FIG. 4 is an x direction, and an up-down direction is a y direction.

$$Gs(x,y)=G1(x,y)-\alpha \times G2(x,y) \tag{1}$$

The visceral fat mass derivation unit 24 derives the visceral fat mass. Therefore, the visceral fat mass derivation unit 24 derives the fat mass distribution in the soft part image Gs by deriving the fat mass for each pixel of the soft part image Gs. Here, a soft tissue in a human body includes a muscle tissue, a fat tissue, blood, and water. In the visceral fat mass derivation unit 24 according to the first embodiment, a tissue other than the fat tissue in the soft tissue is regarded as the muscle tissue. That is, in the visceral fat mass derivation unit 24 according to the first embodiment, a non-fat tissue including the blood and the water is regarded as the muscle tissue.

Figure 5:
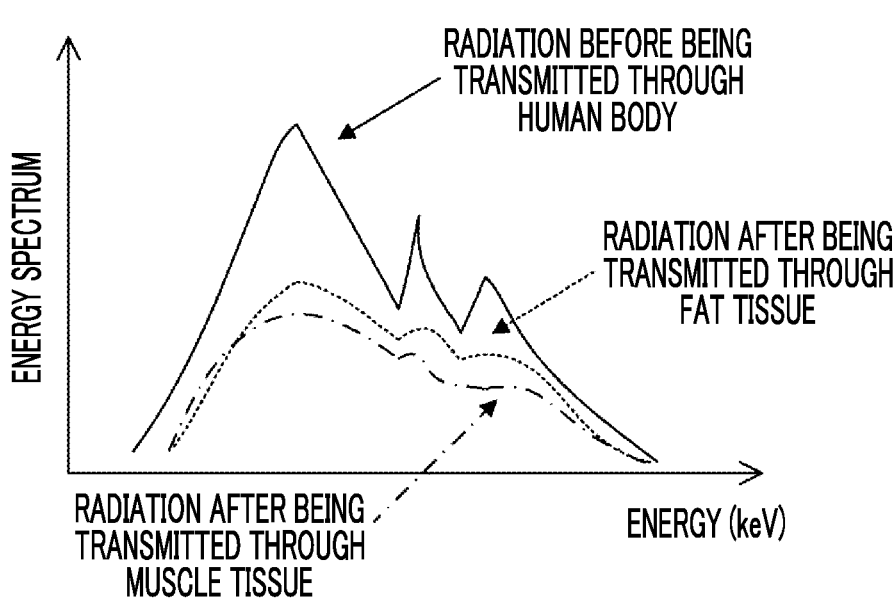
FIG. 5 is a diagram showing an example of energy spectra of radiation after being transmitted through a muscle tissue and radiation after being transmitted through a fat tissue.

The visceral fat mass derivation unit 24 separates muscle and fat in the soft part image Gs by using a difference in an energy characteristic between the muscle tissue and the fat tissue. Here, the dose of the radiation after being transmitted through the subject H, which is the human body, is lower than the dose of the radiation before being incident on the subject H. In addition, since the energy absorbed by the muscle tissue and the energy absorbed by the fat tissue is different and attenuation coefficients are different, the energy spectra of the radiation after being transmitted through the muscle tissue and the radiation after being transmitted through the fat tissue in the radiation after being transmitted through the subject H are different. As shown in FIG. 5, the energy spectrum of the radiation transmitted through the subject H and emitted to each of the first radiation detector 5 and the second radiation detector 6 depends on a body composition of the subject H, specifically, a ratio between the muscle tissue and the fat tissue. Since the fat tissue is more likely to transmit the radiation than the muscle tissue, the dose of the radiation after being transmitted through the human body is smaller in a case in which the ratio of the muscle tissue is larger than the ratio of the fat tissue.

Therefore, the visceral fat mass derivation unit 24 separates muscle and fat from the soft part image Gs by using the difference in the energy characteristic between the muscle tissue and the fat tissue described above. Moreover, the visceral fat mass derivation unit 24 generates a fat image from the soft part image Gs, and derives the fat mass of each pixel based on a pixel value of the fat image.

Note that a specific method by which the visceral fat mass derivation unit 24 separates muscle and fat from the soft part image Gs is not limited, but as an example, the visceral fat mass derivation unit 24 according to the first embodiment generates a fat image Gf from the soft part image Gs by Expression (2) and Expression (3). Specifically, first, the visceral fat mass derivation unit 24 derives a fat percentage $rf(x,y)$ at each pixel position $(x,y)$ in the soft part image Gs by Expression (2). Note that, in Expression (2), $\mu m$ is a weighting coefficient depending on an attenuation coefficient of the muscle tissue, and $\mu f$ is a weighting coefficient depending on an attenuation coefficient of the fat tissue. In addition, $\Delta(x,y)$ represents a concentration difference distribution. The concentration difference distribution is a distribution of a concentration change on the image, which is seen from a concentration obtained by making the radiation reach the first radiation detector 5 and the second radiation detector 6 without being transmitted through the subject H. The distribution of the concentration change on the image is calculated by subtracting the concentration of each pixel in the region of the subject H from the concentration in a blank region obtained by directly irradiating the first radiation detector 5 and the second radiation detector 6 with the radiation in the soft part image Gs.

$$rf(x,y)=\{\mu m-\Delta(x,y)/T(x,y)\}/(\mu m-\mu f) \qquad (2)$$

Moreover, the visceral fat mass derivation unit 24 generates a fat image Gf from the soft part image Gs by Expression (3). Note that, in Expression (3), $(x,y)$ is the pixel position of the fat image Gf and corresponds to the pixel position of the soft part image Gs.

$$Gf(x,y)=rf(x,y)\times Gs(x,y) \qquad (3)$$

In the present embodiment, the visceral fat mass derivation unit 24 derives the pixel value $Gf(x,y)$ of the fat image Gf as the fat mass. In the fat image Gf, the brightness is increased as the fat mass is increased, and the pixel value $Gf(x,y)$ of the fat image Gf is information representing a relative difference in fat between the positions of the subject H. Note that, since the pixel value $Gf(x,y)$ does not represent the true fat mass, as shown in Expression (4), the visceral fat mass derivation unit 24 may derive the true fat mass $F(x,y)$ ($g/cm^2$) for each pixel of the fat image Gf by multiplying each pixel value $Gf(x,y)$ of the fat image Gf by a coefficient $K1(x,y)$ representing the relationship between the predetermined pixel value and the fat mass. In addition, the fat percentage $rf(x,y)$ for each pixel may be used as the fat mass. Note that, in the following description, the pixel value $Gf(x,y)$ is used as the fat mass.

$$F(x,y)=K1(x,y)\times Gf(x,y) \qquad (4)$$

The visceral fat mass derivation unit 24 derives the fat mass distribution in the fat image Gf. Therefore, the visceral fat mass derivation unit 24 derives the fat mass distribution in each line of the fat image Gf in an x-axis direction. The fat mass distribution in the line of the fat image Gf in the x-axis direction represents the fat mass distribution in a cross section perpendicular to a body axis of the subject H.

Figure 6:
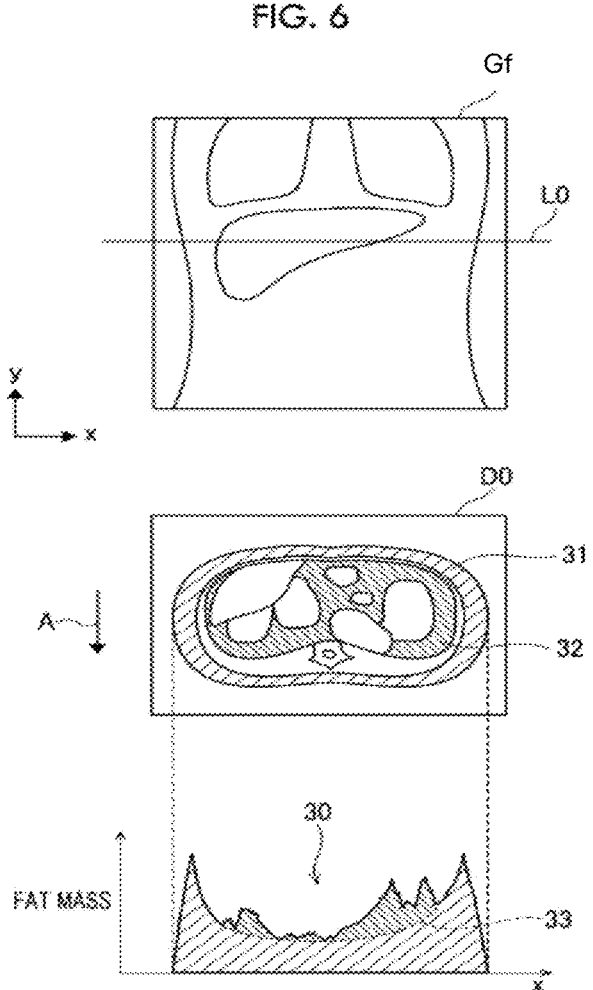
FIG. 6 is a diagram for describing a fat mass distribution.

FIG. 6 is a diagram for describing the fat mass distribution in the line extending in the x-axis direction in the fat image Gf. Note that, for the sake of description, FIG. 6 shows a tomographic image D0 in the cross section orthogonal to the body axis of the subject H corresponding to a line L0 in the x-axis direction set in the fat image Gf. In a fat mass distribution 30 shown in FIG. 6, a horizontal axis indicates the pixel position of the fat image Gf on the line L0, and a vertical axis indicates the fat mass, that is, the pixel value $Gf(x,y)$ of the fat image Gf.

Since fat included in the subject H is distinguished between subcutaneous fat and visceral fat, the tomographic image D0 shown in FIG. 6 includes a subcutaneous fat region 31 and a visceral fat region 32. Note that, in the tomographic image D0 shown in FIG. 6, a hatching direction varies between the subcutaneous fat region 31 and the visceral fat region 32. Here, a value obtained by integrating a pixel value in the subcutaneous fat region 31 and a pixel value in the visceral fat region 32 of the tomographic image D0 in a direction of an arrow A, which is a front-rear direction of the subject H shown in FIG. 6, corresponds to the fat mass distribution 30. In a case in which only the pixel values of the subcutaneous fat region 31 are integrated in the direction of the arrow A in the tomographic image D0, the fat mass distribution has a maximum value close to the right and left end parts of the subject H, and the fat mass is distributed such that the value is reduced toward the vicinity of the center of the subject H. In FIG. 6, for the sake of description, the fat mass distribution corresponding to the subcutaneous fat in the fat mass distribution 30 is shown by a broken line 33, and the hatching direction varies between a subcutaneous fat distribution and a visceral fat distribution.

Figure 7:
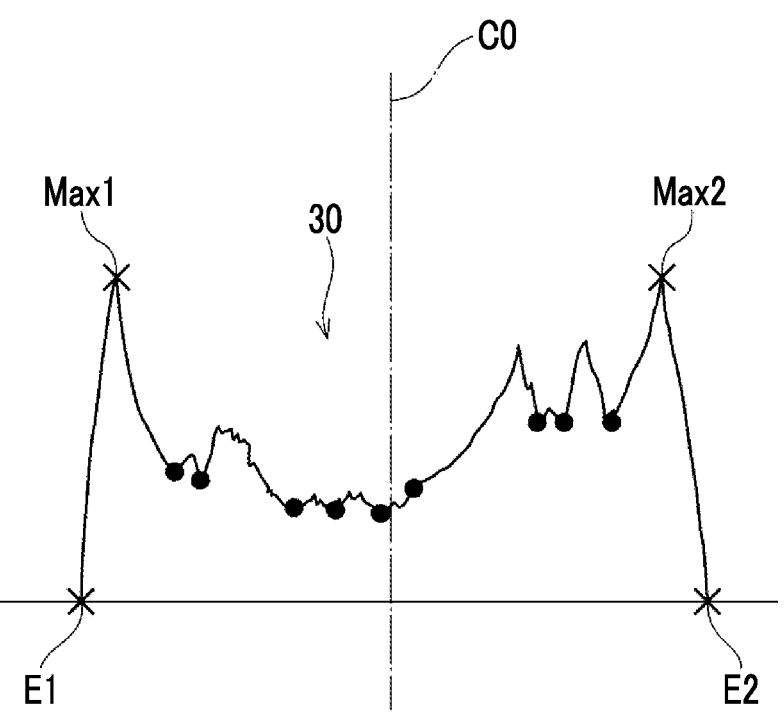
FIG. 7 is a diagram for describing the derivation of subcutaneous fat mass.

The visceral fat mass derivation unit 24 derives the visceral fat mass based on a shape of the fat mass distribution 30. Therefore, the visceral fat mass derivation unit 24 first derives the subcutaneous fat mass. FIG. 7 is a diagram for describing the derivation of the subcutaneous fat mass. The visceral fat mass derivation unit 24 derives the subcutaneous fat mass by using the fact that the subcutaneous fat is distributed symmetrically in the fat mass distribution 30. Therefore, the visceral fat mass derivation unit 24 first detects end points E1 and E2 of the fat mass distribution 30 as shown in FIG. 7. Next, the visceral fat mass derivation unit 24 detects maximum points Max1 and Max2 that first appear in a case in which the fat mass distribution 30 is traced inward from the end points E1 and E2.

Figure 8:
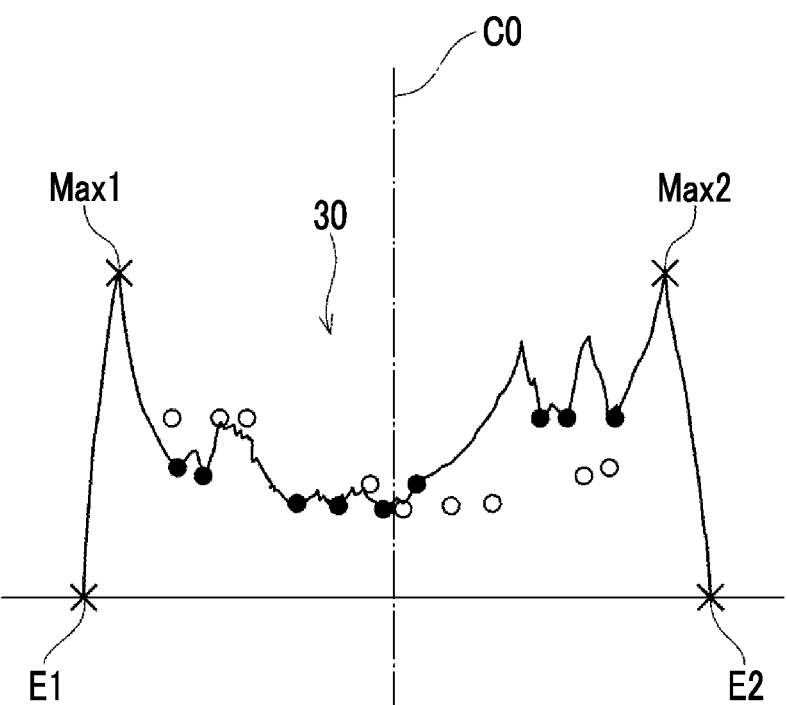
FIG. 8 is a diagram for describing the derivation of the subcutaneous fat mass.

Subsequently, the visceral fat mass derivation unit 24 detects a minimum point of the fat mass distribution 30 between the maximum points Max1 and Max2. In FIG. 7, the minimum point is indicated by a black circle. Note that FIG. 7 shows only some of the minimum points for the sake of description. Next, the visceral fat mass derivation unit 24 sets a center line C0 which bisects the end points E1 and E2 or the maximum points Max1 and Max2. Moreover, as shown in FIG. 8, the visceral fat mass derivation unit 24 sets a correspondence point corresponding to the minimum point at a position symmetrical with respect to the center line C0. In FIG. 8, the correspondence point corresponding to the minimum point is indicated by a white circle.

Figure 9:
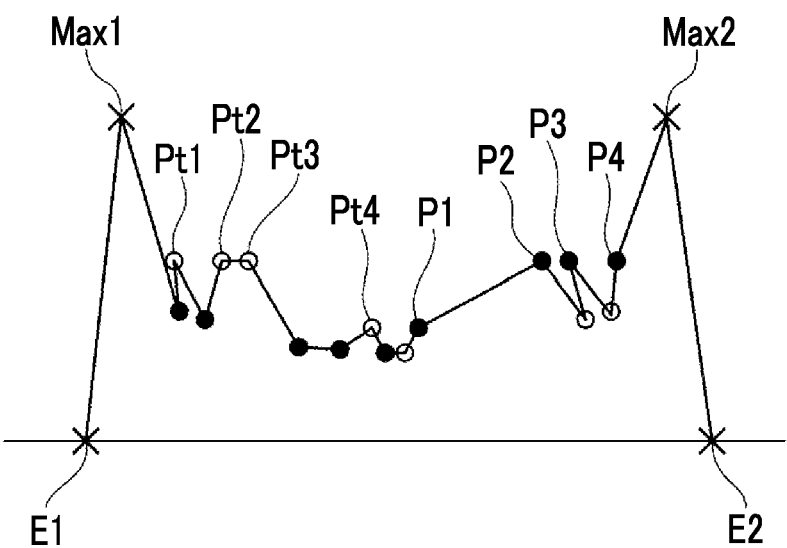
FIG. 9 is a diagram for describing the derivation of the subcutaneous fat mass.
Figure 10:
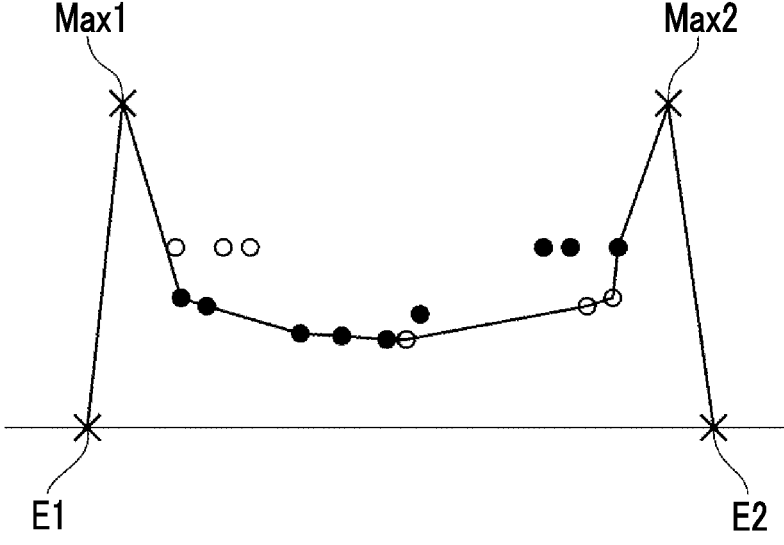
FIG. 10 is a diagram for describing the derivation of a visceral fat mass distribution.

Next, as shown in FIG. 9, the visceral fat mass derivation unit 24 connects the end points E1 and E2, the maximum points Max1 and Max2, the minimum points, and the correspondence points with a line segment. Note that the visceral fat mass derivation unit 24 connects the minimum points and the correspondence points that have positions close to each other in the axial direction with the line segment. Moreover, in a case in which the two line segments intersect with the minimum point and the correspondence point at an upwardly convex angle, the visceral fat mass derivation unit 24 excludes the minimum point and the correspondence point and connects the minimum point and the correspondence point with the line segment again. In FIG. 9, minimum points P1 to P4 and correspondence points Pt1 to Pt4 are excluded. The visceral fat mass derivation unit 24 repeats this processing until there are no intersecting line segments at the upwardly convex angle. In a case in which the minimum points and correspondence points remaining between the maximum point Max1 and the maximum point Max2 are connected with the line segment, as shown in FIG. 10, the remaining minimum points and correspondence points between the maximum point Max1 and the maximum point Max2 are connected to be convex downward.

Figure 11:
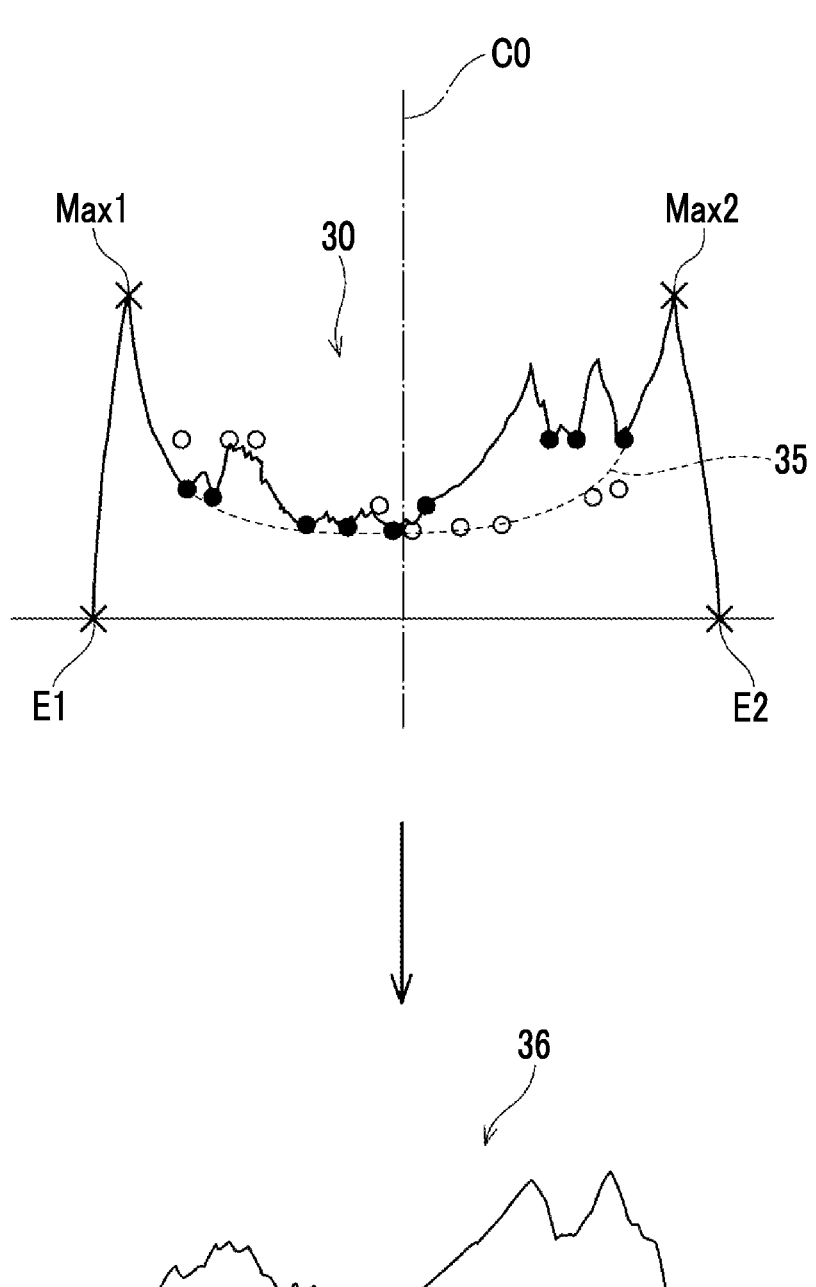
FIG. 11 is a diagram for describing the derivation of the visceral fat mass distribution.

As shown in FIG. 11, the visceral fat mass derivation unit 24 approximates the remaining minimum points and correspondence points between the maximum point Max1 and the maximum point Max2 with a curve 35. For the curve approximation, for example, a method of approximating a quadratic function by the least squares method can be used, but the curve approximation is not limited to this. Moreover, the visceral fat mass derivation unit 24 derives the fat mass distribution 30 above the curve 35 in the fat mass distribution 30 as a visceral fat mass distribution 36. The visceral fat mass distribution 36 is a distribution of pixel values Gv(x,y) representing the visceral fat mass.

Note that the visceral fat mass derivation unit 24 derives the visceral fat mass distribution 36 in all the lines in the x-axis direction in a predetermined region of the fat image Gf, thereby deriving a two-dimensional visceral fat mass distribution in the predetermined region of the fat image Gf as a visceral fat image Gv. The predetermined region may be the entire region of the fat image Gf, or may be a preset region in the fat image Gf. The preset region need only be, for example, a region in a range of ±5 cm from the center line that bisects the fat image Gf to the right and left, but is not limited to this. In addition, the fat image Gf may be displayed, and a region designated by a user in the displayed fat image Gf may be the predetermined region.

In addition, the predetermined region may be a region of a predetermined part detected from the first radiation image G1 or the second radiation image G2. In this case, a region of the abdomen can be the predetermined region. The region of the abdomen can be set by detecting the region from a lower end of a lung field to a hip joint in the radiation image. In this case, the region between the lower end of the lung field and the hip joint can be set as the predetermined region by performing the processing of detecting the lung field and the processing of detecting a bone region on the radiation image.

As a result, the visceral fat image Gv that two-dimensionally represents the visceral fat mass distribution is derived in the predetermined region in the radiation image of the subject H. The pixel value Gv(x,y) of each pixel in the visceral fat image Gv represents the visceral fat mass.

The index value derivation unit 25 derives an index value of the visceral fat mass in the predetermined region of the subject H based on the visceral fat mass distribution represented by the visceral fat image Gv. As the index value, for example, the volume and the weight of the visceral fat can be used. In a case of deriving the volume of the visceral fat, the index value derivation unit 25 derives an area S0 of the visceral fat mass distribution 36 shown in FIG. 11. Moreover, by multiplying the derived area S0 by a size Y0 of one pixel of the fat image Gf in the y-axis direction, volume vi of the visceral fat mass distribution 36 in each line L0 in the x-axis direction is derived. Moreover, the index value derivation unit 25 derives the volume V0 of the visceral fat by integrating all the volume vi derived in all the lines in the x-axis direction in the predetermined region of the fat image Gf. In addition, the index value derivation unit 25 derives the weight of the visceral fat by multiplying the derived volume V0 by standard density of fat.

Figure 12:
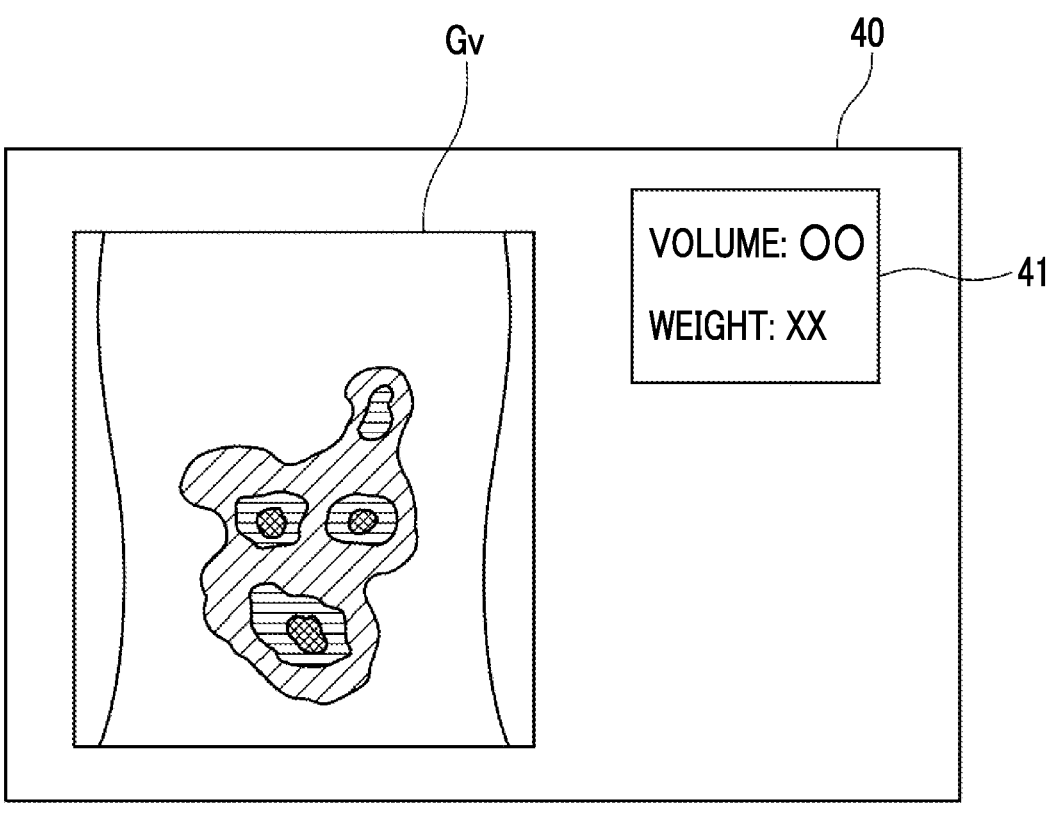
FIG. 12 is a diagram showing a display screen of a visceral fat image.

The display controller 26 displays the visceral fat image Gv on the display 14. FIG. 12 is a diagram showing a display screen of the visceral fat image. As shown in FIG. 12, the visceral fat image Gv is display on a display screen 40. In the visceral fat image Gv, the visceral fat mass distribution is shown by different colors in accordance with the visceral fat mass. Note that, in FIG. 12, the difference in colors is shown by different hatching. In addition, an index value display region 41 is displayed on a right side of the visceral fat image Gv. In the index value display region 41, the volume and the weight derived by the index value derivation unit 25 are displayed.

Then, processing performed in the first embodiment will be described. FIG. 13 is a flowchart showing the processing performed in the first embodiment. The image acquisition unit 21 causes the imaging apparatus 1 to perform the energy subtraction imaging of the subject H to acquire the first and second radiation images G1 and G2 (acquire the radiation image; step ST1). Then, the scattered ray removal unit 22 removes the scattered ray component from the first and second radiation images G1 and G2 (step ST2). In addition, the subtraction unit 23 derives the soft part image Gs in which the soft part of the subject H is extracted from the first and second radiation images G1 and G2 from which the scattered ray component is removed (step ST3).

Subsequently, the visceral fat mass derivation unit 24 derives the fat image Gf and the fat mass distribution 30 from the soft part image Gs (step ST4), and derives the visceral fat mass distribution 36 from the fat mass distribution 30 to derive the visceral fat image Gv (step ST5). Further, the index value derivation unit derives the index value of the visceral fat mass from the visceral fat image Gv (step ST6). Moreover, the display controller 26 displays the visceral fat image Gv representing the visceral fat mass distribution 36 and the index value on the display 14 (step ST7), and the processing is terminated.

As described above, in the present embodiment, the fat mass distribution of the subject H is derived from the radiation image by the energy subtraction processing, and the visceral fat mass distribution of the subject is derived based on the shape of the fat mass distribution in the cross section orthogonal to the body axis of the subject. As described above, in the present embodiment, the radiation image is used without using the CT image, so that the visceral fat mass distribution can be easily acquired.

Then, a second embodiment of the present disclosure will be described. Note that, a derivation method of the visceral fat mass distribution 36 of a fat mass derivation device according to the second embodiment is different from that of the first embodiment, and a device configuration according to the second embodiment is the same as the configuration of the fat mass derivation device 10 according to the first embodiment, and thus the detailed description of the device configuration will be omitted here.

Here, as can be seen from the tomographic image D0 and the fat mass distribution 30 in FIG. 6 described above, the region in the vicinity of the right and left end parts of the fat mass distribution 30 is the subcutaneous fat region. In the second embodiment, the visceral fat mass derivation unit 24 is different from that of the first embodiment in that the visceral fat mass derivation unit 24 derives the visceral fat mass distribution based on the subcutaneous fat region in the fat mass distribution 30.

Figure 14:
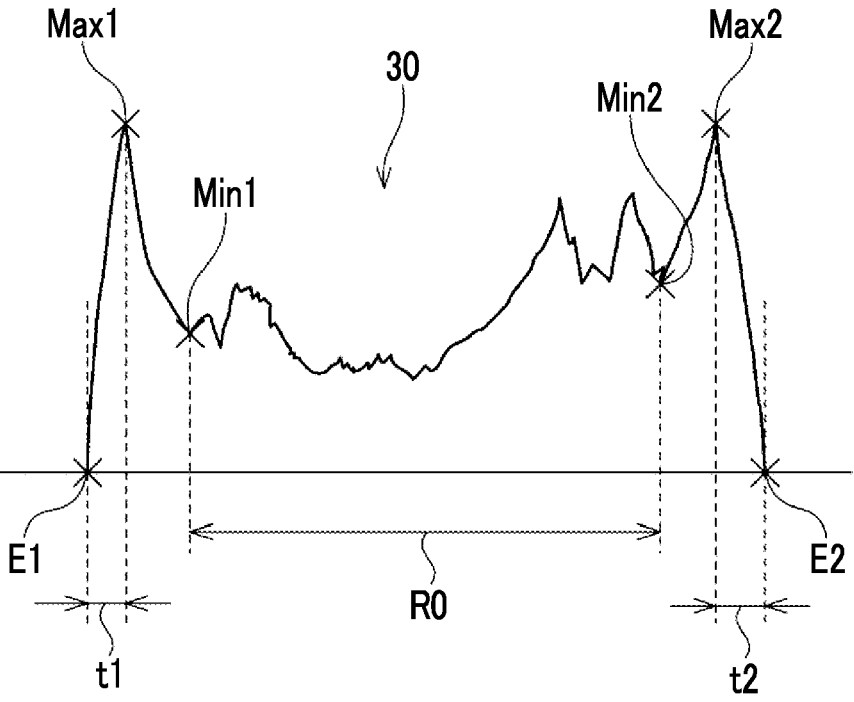
FIG. 14 is a diagram for describing another example of the derivation of the visceral fat mass distribution.

FIG. 14 is a diagram for describing the derivation of the visceral fat mass distribution in the second embodiment. As shown in FIG. 14, the visceral fat mass derivation unit 24 detects the maximum points Max1 and Max2 that first appear in a case in which the fat mass distribution 30 is traced inward from the end points E1 and E2 of the fat mass distribution 30. The maximum points Max1 and Max2 correspond to the positions at which the subcutaneous fat is the thickest in the fat mass distribution 30. Moreover, the visceral fat mass derivation unit 24 derives an average value of a distance t1 from the end point E1 to the maximum point Max1 and a distance t2 from the end point E2 to the maximum point Max2 in the fat mass distribution 30 as a subcutaneous fat thickness of the subject H (hereinafter, referred to as subcutaneous fat thickness t0).

Next, the visceral fat mass derivation unit 24 detects minimum points Min1 and Min2 that first appear in a case in which the fat mass distribution 30 is traced inward from the maximum points Max1 and Max2. The minimum points Min1 and Min2 are points at which the region including only the subcutaneous fat is switched to the region including the subcutaneous fat and the visceral fat. Further, the visceral fat mass derivation unit 24 derives the visceral fat mass distribution by subtracting a value corresponding to the subcutaneous fat thickness t0 from the fat mass distribution 30 in a region R0 between the minimum points Min1 and Min2.

Specifically, the visceral fat mass derivation unit 24 derives a pixel value Q0 of the region directly irradiated with radiation in the first radiation image G1 (or the second radiation image G2) from which the scattered ray component is removed. In a case in which the attenuation coefficient of radiation per unit thickness of fat is $\mu(t)$, a pixel value Q1 obtained by transmitting the radiation through the subcutaneous fat having the thickness of t0 can be calculated $Q1=Q0/exp(\mu(t)\times t0)$. Therefore, a pixel value $\Delta Q$ representing the fat mass corresponding to the subcutaneous fat having the thickness of t0 can be calculated by $\Delta Q=Q0-Q1$. For example, in a case in which $Q0=100000$, $t0=2$ cm, $\mu(t)=0.2$, $Q1=100000/exp(0.2\times2)=67032$, and thus $\Delta Q=100000-67032=32968$ can be obtained. Note that a predetermined value need only be used for the attenuation coefficient $\mu(t)$ of fat.

Moreover, although it is a rough calculation, the visceral fat mass derivation unit 24 derives the visceral fat mass distribution by uniformly subtracting pixel value $\Delta Q$ which is the value corresponding to the subcutaneous fat thickness t0 from the fat mass distribution 30 in a region R0 between the minimum points Min1 and Min2.

Then, a third embodiment of the present disclosure will be described. Note that, a derivation method of the visceral fat mass distribution 36 of a fat mass derivation device according to the third embodiment is different from that of the first embodiment, and a device configuration according to the second embodiment is the same as the configuration of the fat mass derivation device according to the first embodiment, and thus the detailed description of the device configuration will be omitted here.

The visceral fat mass derivation unit 24 of the fat mass derivation device according to the third embodiment is different from that of the first embodiment in that the visceral fat mass derivation unit 24 derives the visceral fat mass distribution from the fat mass distribution by using a trained neural network. Here, the trained neural network consists of, for example, a convolutional neural network, and is constructed by subjecting the convolutional neural network to machine learning by using teacher data including a fat mass distribution for learning and a visceral fat mass distribution which is a correct answer in the fat mass distribution for learning.

Figure 15:
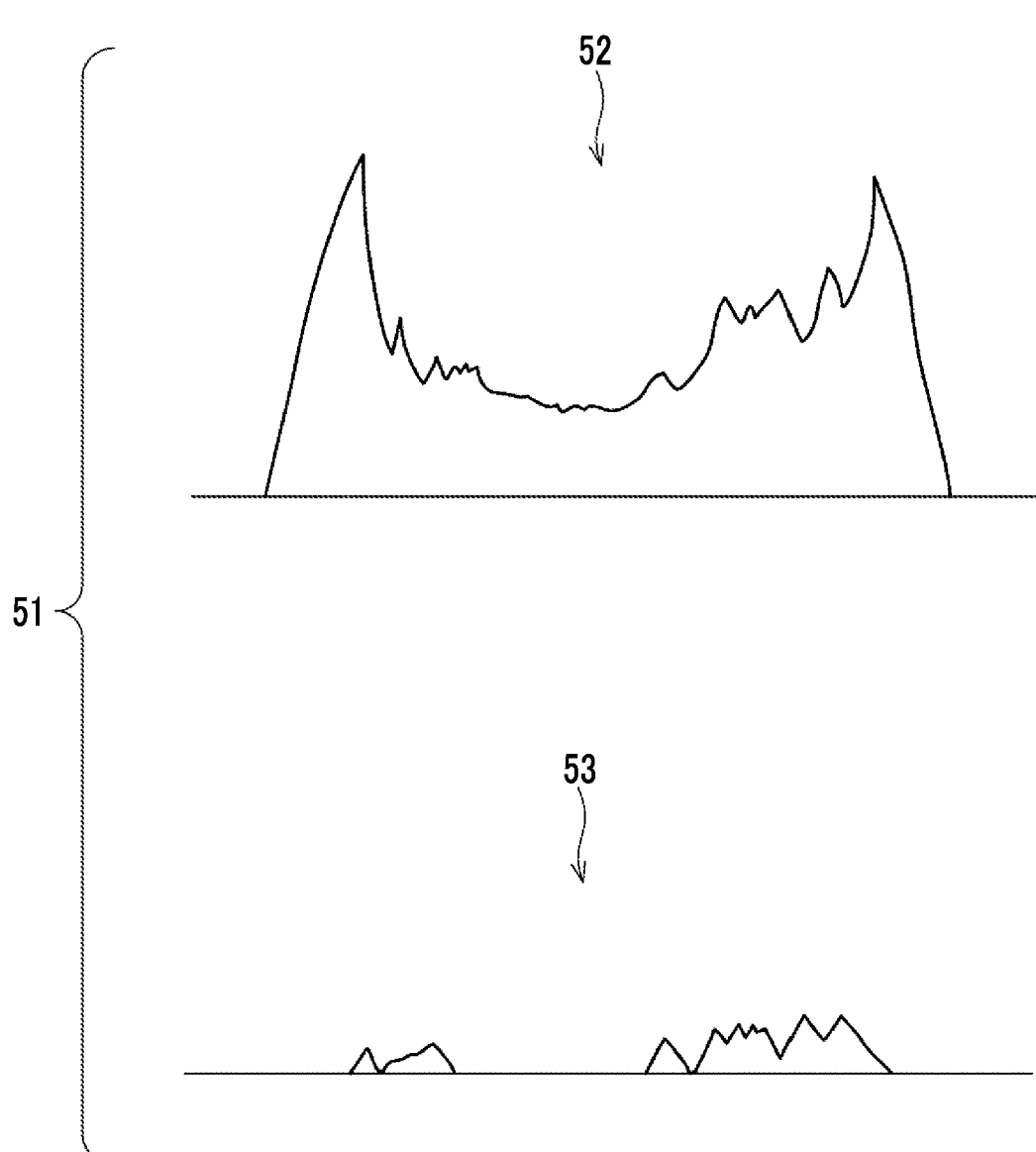
FIG. 15 is a diagram showing teacher data.

FIG. 15 is a diagram showing the teacher data. As shown in FIG. 15, teacher data 51 includes a fat mass distribution for learning 52 and a correct answer visceral fat mass distribution 53 representing the visceral fat mass distribution in the fat mass distribution for learning 52. The fat mass distribution for learning 52 is derived by integrating the signal values of both the subcutaneous fat region and the visceral fat region extracted from the tomographic image included in the CT image in the front-rear direction of the human body. Note that the front-rear direction of the human body corresponds to an imaging direction of the energy subtraction imaging, that is, a direction in which the subject H is irradiated with the radiation. The fat mass distribution for learning 52 is derived by integrating the signal value of the visceral fat region extracted from the tomographic image included in the CT image in the front-rear direction of the human body.

Moreover, the convolutional neural network is trained by inputting the fat mass distribution for learning 52 to the convolutional neural network, deriving a difference between the visceral fat mass distribution and the correct answer visceral fat mass distribution 53 output from the convolutional neural network as a loss, and correcting the parameter of the convolutional neural network such that the loss is reduced. Moreover, the trained neural network is constructed by repeating the learning until the loss reaches a predetermined threshold value. In this case, the convolutional neural network learns shape characteristics of the fat mass distribution and the visceral fat mass distribution.

In the third embodiment, the visceral fat mass derivation unit 24 derives the visceral fat mass distribution from the fat mass distribution 30 derived by the visceral fat mass derivation unit 24 by using the trained neural network. As described above, it is also possible to derive the visceral fat mass distribution by using the trained neural network.

Note that, in each of the embodiments described above, the index value derivation unit 25 derives at least one of the volume or the weight of the visceral fat in the predetermined region of the fat image Gf as the index value, but the index value is not limited to this. By acquiring the information on body weight of the subject H and dividing the weight of the visceral fat by the body weight of the subject H, the visceral fat percentage of the subject H may be derived as the index value. In this case, as the body weight of the subject H, it is preferable to use the body weight of a predetermined region from which the visceral fat mass distribution in the fat image Gf is derived. The body weight of the predetermined region is derived as follows.

First, the index value derivation unit 25 derives volume Vh0 of the predetermined region of the subject H by integrating the body thickness distribution T(x,y) derived by the scattered ray removal unit 22 in the predetermined region of the fat image Gf. In addition, the index value derivation unit 25 derives volume vai of the fat mass distribution 30 in each line L0 extending in the x-axis direction by deriving the area of the fat mass distribution 30 in each line L0 in the x-axis direction in the predetermined region of the fat image Gf, and multiplying the derived area by the size Y0 of one pixel of the fat image Gf in the y-axis direction. Moreover, the index value derivation unit 25 derives volume Vh1 of the fat by integrating all the volume vai derived for the x-axis direction in the predetermined region of the fat image Gf. In addition, the index value derivation unit 25 derives volume Vh2 of the tissue other than fat, such as muscle, blood, and water, of the subject H by subtracting the volume Vh1 of fat from the volume Vh0 of the subject H.

Moreover, the index value derivation unit 25 derives the body weight of the subject H in the predetermined region by calculating Vh1×standard density of fat+Vh2×standard density of tissue other than fat. Note that, as the standard density of the tissue other than fat, for example, the density of water need only be used.

In addition, in each of the embodiments described above, the visceral fat image of the subject H and the index value of the visceral fat mass may be stored in an image storage server (not shown). In this case, in the fat mass derivation device according to the present embodiment, the image acquisition unit 21 may acquire a past visceral fat image of the same subject H from the image storage server, and may display a current visceral fat image and the past visceral fat image in a comparable manner. In addition, the image acquisition unit 21 may acquire an index value of the past visceral fat mass of the same subject H from the image storage server, and may display a change of the index value based on the index value of the current visceral fat mass and the index value of the past visceral fat mass as a graph. Here, the index value of the past visceral fat mass is an example of a past index value.

Figure 16:
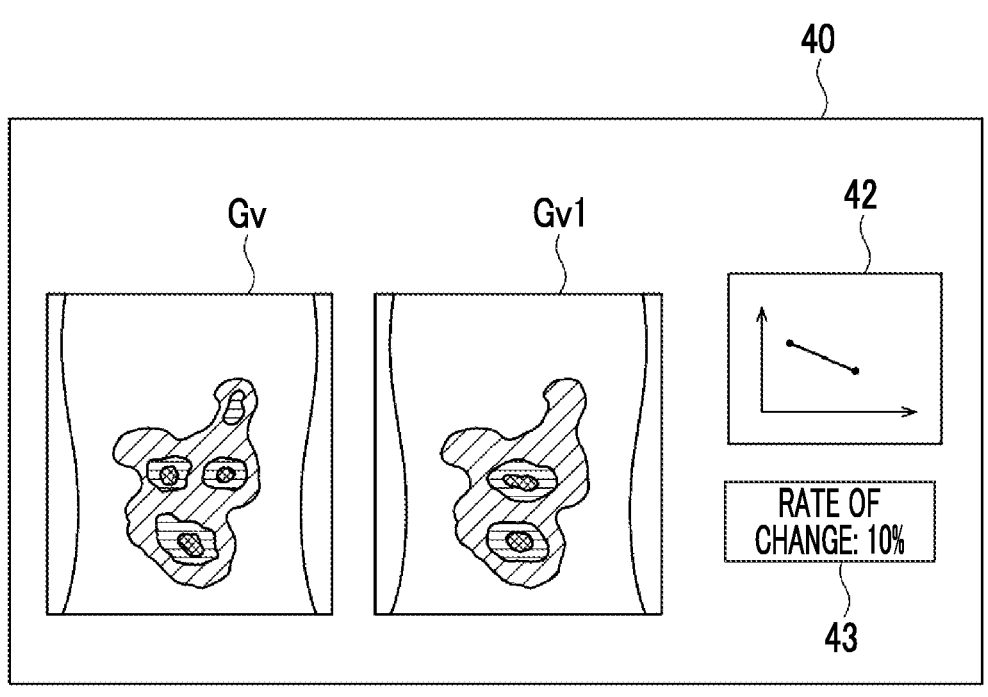
FIG. 16 is a diagram showing another example of the display screen of the visceral fat image.

FIG. 16 is a diagram showing a display screen of the current visceral fat image and the past visceral fat image. As shown in FIG. 16, the display screen 40 displays a current visceral fat image Gv and a past visceral fat image Gv1 in a comparable manner by the current visceral fat image Gv and the past visceral fat image Gv1 side by side. Note that the current visceral fat image Gv and the past visceral fat image Gv1 may be displayed in a switchable manner by an operation from the input device 15. As described above, in a case of displaying the current visceral fat image Gv and the past visceral fat image Gv1, the index value derivation unit 25 may derive a graph representing a transition of the change of the visceral fat mass based on the index value of the current visceral fat mass and the index value of the past visceral fat mass, and may display the derived graph. Further, a rate of change may be derived as the index value. In FIG. 16, a graph 42 and a rate of change 43 derived by the index value derivation unit 25 are displayed.

Figure 17:
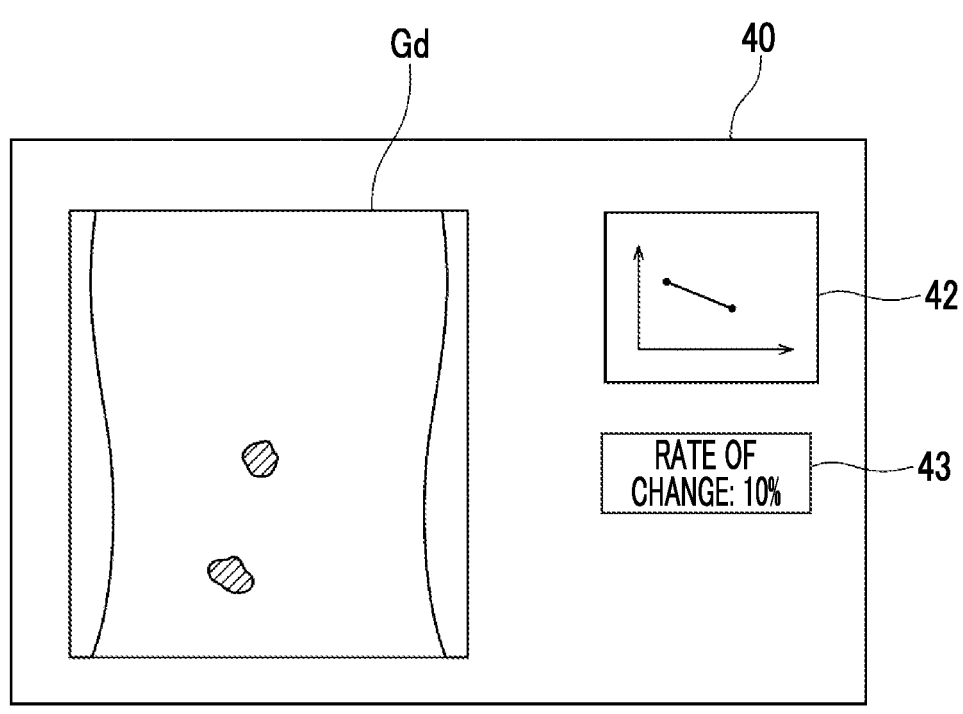
FIG. 17 is a diagram showing a display screen of a change amount image.

Note that, in a case in which the past visceral fat image is acquired, a difference value between the corresponding pixels of the current visceral fat image Gv and the past visceral fat image Gv1 may be derived as a change amount of the visceral fat mass. In this case, a change amount image representing the change amount may be displayed on the display 14. FIG. 17 is a diagram showing a display screen of the change amount image. As shown in FIG. 17, on the display screen 40, instead of the current visceral fat image Gv and the past visceral fat image Gv1, a change amount image Gd representing the change amount between the current visceral fat image Gv and the past visceral fat image Gv1 is displayed. Note that, in addition to the visceral fat image Gv and the past visceral fat image Gv1 shown in FIG. 16, the change amount image Gd may be displayed.

In addition, in each of the embodiments described above, in a case in which the maximum point and the minimum point of the pixel value of the fat mass in the fat mass distribution 30, that is, the fat image Gf, are obtained, the fat mass distribution 30 may be smoothed in order to reduce the influence of the pixel value greatly fluctuating in units of one pixel due to the influence of random noise. For example, the maximum point and the minimum point may be obtained by calculating a movement average of the pixel values with surrounding pixels for each pixel of the fat mass distribution 30 in the x-axis direction and using the movement average as the pixel value of each pixel to smooth the fat mass distribution 30. In this case, a pixel width for obtaining the movement average need only be, for example, 3 to 13 pixels.

In addition, in each of the embodiments described above, the first and second radiation images G1 and G2 are acquired by the one-shot method in a case in which the energy subtraction processing is performed for deriving the fat image, but the present disclosure is not limited to this. The first and second radiation images G1 and G2 may be acquired by a so-called two-shot method in which imaging is performed twice by using only one radiation detector. In a case of the two-shot method, there is a possibility that a position of the subject H included in the first radiation image G1 and the second radiation image G2 shifts due to a body movement of the subject H. Therefore, in the first radiation image G1 and the second radiation image G2, it is preferable to perform the processing according to the present embodiment after registration of the subject is performed.

In addition, in each of the embodiments described above, the visceral fat mass distribution is derived by using the first and second radiation images acquired by the system that images the subject H by using the first and second radiation detectors 5 and 6, but the visceral fat mass distribution may be derived from the first and second radiation images G1 and G2 acquired by using an accumulative phosphor sheet instead of the radiation detector. In this case, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case in which the first and second radiation images G1 and G2 are acquired by using the accumulative phosphor sheet.

In addition, the radiation in each of the embodiments described above is not particularly limited, and α-rays or γ-rays can be used in addition to X-rays.

In addition, in each of the embodiments described above, various processors shown below can be used as the hardware structure of processing units that execute various pieces of processing, such as the image acquisition unit 21, the scattered ray removal unit 22, the subtraction unit 23, the visceral fat mass derivation unit 24, the index value derivation unit 25, and the display controller 26. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute a specific processing, such as an application specific integrated circuit (ASIC).

One processing unit may be configured by one of these various processors, or may be configured by a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structure of these various processors, more specifically, it is possible to use an electrical circuit (circuitry) in which circuit elements, such as semiconductor elements, are combined.

What is claimed is:

1. A fat mass derivation device comprising:
at least one processor,
wherein the processor
derives a fat mass distribution of a subject from a first radiation image and a second radiation image acquired by imaging the subject with radiation having different energy distributions,
derives a visceral fat mass distribution of the subject based on a shape of the fat mass distribution in a cross section orthogonal to a body axis of the subject,
derives the fat mass distribution of the subject from the first radiation image and the second radiation image acquired by imaging the subject from a front surface or a rear surface,
derives the visceral fat mass distribution by separating the fat mass distribution into a subcutaneous fat mass distribution and the visceral fat mass distribution based on minimum points of the fat mass distribution and symmetry of the fat mass distribution,
detects both end points of the fat mass distribution,
detects maximum points that first appear in a case in which the fat mass distribution is traced inward from the end points,
sets a center line which bisects the end points or the maximum points,
sets correspondence points corresponding to the minimum points at a position symmetrical with respect to the center line,
connects the end points, the maximum points, the minimum points, and the correspondence points with line segments,
in a case in which the two line segments intersect with the minimum point and the correspondence point at an upwardly convex angle, excludes the minimum point and the correspondence point and connects the minimum point and the correspondence point with the line segment again,
repeats connecting processing until there are no intersecting line segments at the upwardly convex angle,
approximates remaining minimum points and correspondence points between the maximum points with a curve, and derives the fat mass distribution above the curve in the fat mass distribution as the visceral fat mass distribution.

2. The fat mass derivation device according to claim 1, wherein the processor
derives an interval between at least one end part of the fat mass distribution and a maximum point closest to the end part as a subcutaneous fat thickness of the subject, and
derives the visceral fat mass distribution from the fat mass distribution based on the subcutaneous fat thickness.

3. The fat mass derivation device according to claim 1, wherein the processor displays a visceral fat image representing the visceral fat mass distribution.

4. The fat mass derivation device according to claim 3, wherein the processor
acquires a past visceral fat image for the same subject, and
displays the visceral fat image and the past visceral fat image in a comparable manner.

5. The fat mass derivation device according to claim 3, wherein the processor
acquires a past visceral fat image for the same subject, and
displays a change amount of the visceral fat image from the past visceral fat image.

6. The fat mass derivation device according to claim 1, wherein the processor
derives an index value of visceral fat mass in a predetermined region of the subject based on the visceral fat mass distribution, and
displays the index value.

7. The fat mass derivation device according to claim 6, wherein the index value is at least one of volume or weight of the visceral fat mass.

8. The fat mass derivation device according to claim 6, wherein the index value is a visceral fat percentage of the subject.

9. The fat mass derivation device according to claim 1, wherein the processor
acquires a past index value which is at least one past index value of the subject, and
displays a change of the index value based on the index value and the past index value as a graph.

10. The fat mass derivation device according to claim 1, wherein the processor derives a smoothed fat mass distribution.

11. The fat mass derivation device according to claim 1, wherein the processor derives the visceral fat mass distribution from the fat mass distribution by using a trained neural network, and
the trained neural network is trained by using teacher data including a fat mass distribution for learning and a visceral fat mass distribution which is a correct answer in the fat mass distribution for learning.

12. A fat mass derivation method comprising:
deriving a fat mass distribution of a subject from a first radiation image and a second radiation image acquired by imaging the subject with radiation having different energy distributions;
deriving a visceral fat mass distribution of the subject based on a shape of the fat mass distribution in a cross section orthogonal to a body axis of the subject;

deriving the fat mass distribution of the subject from the first radiation image and the second radiation image acquired by imaging the subject from a front surface or a rear surface;

deriving the visceral fat mass distribution by separating the fat mass distribution into a subcutaneous fat mass distribution and the visceral fat mass distribution based on minimum points of the fat mass distribution and symmetry of the fat mass distribution;

detects both end points of the fat mass distribution;

detects maximum points that first appear in a case in which the fat mass distribution is traced inward from the end points;

sets a center line which bisects the end points or the maximum points;

sets correspondence points corresponding to the minimum points at a position symmetrical with respect to the center line;

connects the end points, the maximum points, the minimum points, and the correspondence points with line segments;

in a case in which the two line segments intersect with the minimum point and the correspondence point at an upwardly convex angle, excludes the minimum point and the correspondence point and connects the minimum point and the correspondence point with the line segment again;

repeats connecting processing until there are no intersecting line segments at the upwardly convex angle;

approximates remaining minimum points and correspondence points between the maximum points with a curve; and derives the fat mass distribution above the curve in the fat mass distribution as the visceral fat mass distribution.

13. A non-transitory computer-readable storage medium that stores a fat mass derivation program causing a computer to execute:

a procedure of deriving a fat mass distribution of a subject from a first radiation image and a second radiation image acquired by imaging the subject with radiation having different energy distributions;

a procedure of deriving a visceral fat mass distribution of the subject based on a shape of the fat mass distribution in a cross section orthogonal to a body axis of the subject;

a procedure of deriving the fat mass distribution of the subject from the first radiation image and the second radiation image acquired by imaging the subject from a front surface or a rear surface;

a procedure of deriving the visceral fat mass distribution by separating the fat mass distribution into a subcutaneous fat mass distribution and the visceral fat mass distribution based on minimum points of the fat mass distribution and symmetry of the fat mass distribution;

a procedure of detecting both end points of the fat mass distribution;

a procedure of detecting maximum points that first appear in a case in which the fat mass distribution is traced inward from the end points;

a procedure of setting a center line which bisects the end points or the maximum points;

a procedure of setting correspondence points corresponding to the minimum points at a position symmetrical with respect to the center line;

a procedure of connecting the end points, the maximum points, the minimum points, and the correspondence points with line segments;

in a case in which the two line segments intersect with the minimum point and the correspondence point at an upwardly convex angle, a procedure of excluding the minimum point and the correspondence point and connecting the minimum point and the correspondence point with the line segment again;

a procedure of repeating connecting processing until there are no intersecting line segments at the upwardly convex angle;

a procedure of approximating remaining minimum points and correspondence points between the maximum points with a curve; and a procedure of deriving the fat mass distribution above the curve in the fat mass distribution as the visceral fat mass distribution.

* * * * *